US005387411A

United States Patent [19]

Abrutyn et al.

[11] Patent Number: 5,387,411

[45] Date of Patent: Feb. 7, 1995

[54] ANTIPERSPIRANT CONTAINING A HYDROPHOBIC MACROPOROUS POLYMER AS THE SUSPENDING AGENT

[75] Inventors: Eric S. Abrutyn, Midland, Mich.; Tina M. Gressani, Wappinger Falls, N.Y.

[73] Assignee: Dow Corning Corporation, Midland, Mich.

[21] Appl. No.: 593,821

[22] Filed: Oct. 5, 1990

[51] Int. Cl.[6] .......................... A61K 7/32; A61K 7/34; A61K 7/38; A61K 9/12

[52] U.S. Cl. ............................... 424/47; 424/DIG. 5; 424/65; 424/66; 424/67; 424/68; 424/69; 424/76.2; 424/76.21

[58] Field of Search .............................. 424/47, 68, 81

[56] References Cited

U.S. PATENT DOCUMENTS

| | | | |
|---|---|---|---|
| 3,966,902 | 6/1976 | Chromocek | 424/81 |
| 4,090,013 | 5/1978 | Ganslaw et al. | 424/78 |
| 4,587,129 | 6/1986 | Kliment | 512/4 |
| 4,659,564 | 4/1987 | Cox et al. | 424/68 |
| 4,664,847 | 5/1987 | Williams | 424/40 |
| 4,690,825 | 9/1987 | Won | 424/501 |
| 4,719,040 | 1/1988 | Traas | 512/4 |
| 4,724,240 | 2/1988 | Abrutyn | 514/847 |
| 4,764,362 | 8/1988 | Barchas | 424/61 |
| 4,776,358 | 10/1988 | Korsk | 132/321 |
| 4,806,360 | 2/1989 | Leong | 424/487 |
| 4,813,976 | 3/1989 | Barchas | 51/293 |
| 4,855,127 | 8/1989 | Abrutyn | 424/411 |
| 4,855,144 | 8/1989 | Leong | 424/487 |
| 4,870,145 | 9/1989 | Chromecek | 526/217 |
| 4,873,091 | 10/1989 | Jankower | 424/489 |
| 4,880,617 | 11/1989 | Chromecek | 424/501 |
| 4,881,490 | 11/1989 | Ducharme | 119/1 |
| 4,883,021 | 11/1989 | Ducharme | 119/1 |
| 4,898,913 | 2/1990 | Ziemelis | 525/301 |
| 4,904,524 | 2/1990 | Yoh | 428/311 |
| 4,923,894 | 5/1990 | Kanda | 514/493 |
| 4,933,372 | 6/1990 | Feibush | 521/91 |
| 4,948,818 | 8/1990 | Carmody | 521/149 |
| 4,958,999 | 9/1990 | Liscomb | 425/110 |
| 4,961,532 | 10/1990 | Tangney | 239/60 |
| 4,962,133 | 10/1990 | Chromecek | 521/56 |

FOREIGN PATENT DOCUMENTS

| | | | |
|---|---|---|---|
| 1168157 | 5/1984 | Canada | 514/847 |
| 61701 | 10/1982 | European Pat. Off. | 514/847 |
| 306236 | 3/1989 | European Pat. Off. | 514/847 |
| 8702013 | 2/1988 | WIPO | 514/847 |
| 8910132 | 11/1989 | WIPO | 514/847 |

*Primary Examiner*—Dale R. Ore
*Attorney, Agent, or Firm*—James L. DeCesare

[57] ABSTRACT

An antiperspirant composition containing an astringent compound, a volatile carrier, and a suspending agent for the astringent compound. The improvement relates to incorporating into the composition as the suspending agent a hydrophobic macroporous highly crosslinked polymer. The hydrophobic macroporous polymer is free of "in situ" entrapped active ingredients. The preferred antiperspirant product is a roll-on formulation.

14 Claims, 3 Drawing Sheets

1500X

2000X

1500X

ANTIPERSPIRANT CONTAINING A HYDROPHOBIC MACROPOROUS POLYMER AS THE SUSPENDING AGENT

BACKGROUND OF THE INVENTION

This invention relates to an antiperspirant composition which includes a hydrophobic macroporous highly cross-linked polymer. More particularly, the invention includes an antiperspirant product that contains small porous polymer particles which are free of any "in situ" entrapped active ingredient, and which particles function as the suspending agent for the astringent antiperspirant compound.

The concept of producing spheres and beads of a macroporous polymer is old in the art, as well as the use of such macroporous structures for the entrapment and subsequent delivery of certain active ingredients. One example of this concept may be found in U.S. Pat. No. 4,690,825, issued Sep. 1, 1987, in which a suspension polymerization process is employed to produce beads from a monomer system including styrene and divinylbenzene. Mineral oil is entrapped "in situ" and the beads are said to possess utility in various cosmetic applications. In U.S. Pat. No. 4,719,040, issued Jan. 12, 1988, a macroporous polymer laden with perfume is incorporated into an air freshener gel. U.S. Pat. No. 4,724,240, issued Feb. 9, 1988, European Patent No. 61,701, granted Jul. 16, 1986, and Canadian Patent No. 1,168,157, issued May 29, 1984, each relate to "in situ" entrapped emollients and moisturizers carried within macroporous beads. Various cosmetic and toiletry applications of these products are disclosed.

A macroporous polymer entrapping an emollient is taught in U.S. Pat. No. 4,764,362, issued Aug. 16, 1988, and in U.S. Pat. No. 4,813,976, issued Mar. 21, 1989, in which the polymer is incorporated into a nail conditioning emery board. During filing of the nails, the emollient is released in order to condition and lubricate the nails. A similar concept is taught in U.S. Pat. No. 4,776,358, issued Oct. 11, 1988, in which a dental floss includes flavor oils entrapped in certain "microsponges". Suspension polymerized macroporous polymer beads are taught in U.S. Pat. No. 4,806,360, issued Feb. 21, 1989, and in U.S. Pat. No. 4,855,144, issued Aug. 8, 1989, wherein melanin pigment is incorporated into the macroporous structure and applied to the skin and said to function as a sunscreen. Similar bead structures are also taught in European Patent Application Publication No. 306 236A2, published Mar. 3, 1989, and in Patent Cooperation Treaty International Publication No. WO 88/01164, published Feb. 25, 1988.

A reticulated polyurethane foam is disclosed in U.S. Pat. No. 4,828,542, issued May 9, 1989, having macroporous polymer particles bonded to the foam. The particles entrap a liquid soap and the foam functions as a cleaning pad. In U.S. Pat. No. 4,855,127, issued Aug. 8, 1989, and U.S. Pat. No. 4,880,617, issued Nov. 14, 1989, hydrophobic polymeric porous beads are used as a free-flowing solid carrier for various pheromones, pesticides, fragrances, and chemicals entrapped therein. Hydrophilic beads are formed in U.S. Pat. No. 4,870,145, issued Sep. 26, 1989, and upon removal of the solvent used to form the voids, the beads possess various utilities including incorporation into contact lens cleaners, facial scrubs, and tile cleaners. In U.S. Pat. No. 4,873,091, issued Oct. 10, 1989, resilient microbeads are formed by suspension polymerizing curable elastomers such as isoprene rubbers to produce porous rubber beads. The porous rubber beads are employed in topical applications. In the Patent Cooperation Treaty International Publication No. WO89/10132, published Nov. 2, 1989, porous particles are disclosed as an ingredient in personal care emulsions. A pet litter is described in U.S. Pat. No. 4,881,490, issued Nov. 21, 1989, and U.S. Pat. No. 4,883,021, issued Nov. 28, 1989, wherein a macromolecular polymer entrapping a fragrance is incorporated in an animal litter to slowly release fragrance for combating odors.

In U.S. Pat. No. 4,898,913, issued Feb. 6, 1990, macroporous hydrophobic powder materials are rendered hydrophilic by treatment of the surface of the powder. In one embodiment of the '913 patent, the surface is saponified whereas in another embodiment an acrylate monomer is polymerized on the surface. A wet wipe useful in personal care applications is disclosed in U.S. Pat. No. 4,904,524, issued Feb. 27, 1990, wherein macroporous polymeric beads containing a silicone skin conditioner are incorporated into the surface of a paper sheet. Polymeric microparticles loaded with a fungicide are taught in U.S. Pat. No. 4,923,894, issued May 8, 1990. In U.S. Pat. No. 4,933,372, issued Jun. 12, 1990, there is described rigid resin particles formed by polymerizing monounsaturated and polyunsaturated monomers within the pores of inorganic template particles such as silica gel, silica, alumina, zirconia, and metal oxides. The template particles are dissolved leaving porous adsorptive particles which mirror the template particles in size, surface area, and porosity.

In accordance with the present invention however, an antiperspirant composition is formed containing hydrophobic macroporous polymer particles which are free of any "in situ" entrapped active ingredient in contrast to the prior art. The empty macroporous particles function as a suspending agent in the antiperspitant composition and prevent settling of the astringent compound.

SUMMARY OF THE INVENTION

This invention is directed to an antiperspirant composition containing as components thereof at least one material selected from the group consisting of astringent antiperspirant compounds, a volatile carrier, a suspending agent, emollients, perfumes, and other ingredients normally used in making antiperspirant products. The improvement relates to the concept of incorporating into the composition as the suspending agent a hydrophobic macroporous highly crosslinked polymer. The hydrophobic macroporous polymer is free of "in situ" entrapped active ingredients.

These and other objects, features, and advantages, of the present invention will become apparent when considered in light of the following detailed description including the accompanying drawings.

IN THE DRAWINGS

Figures 1, 2:
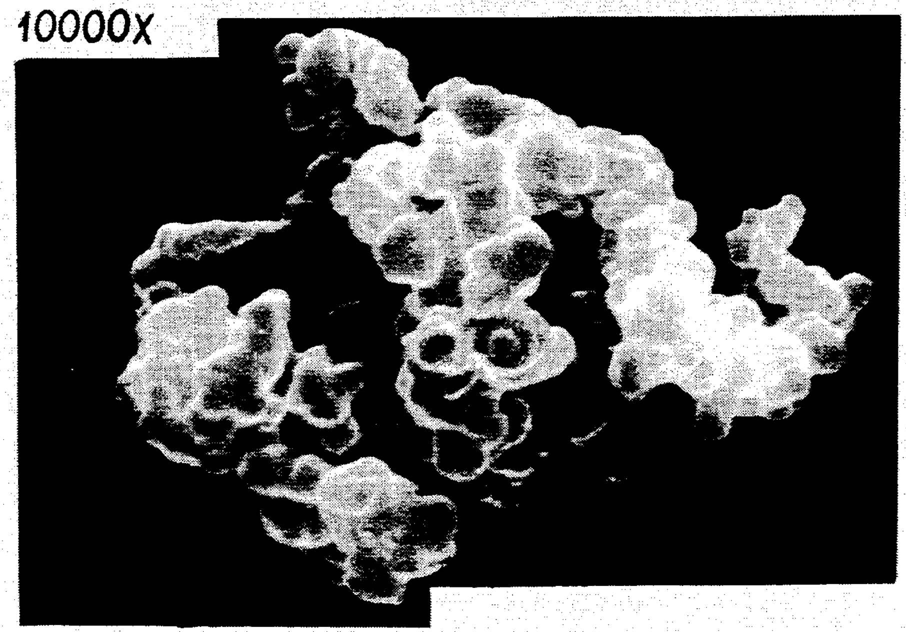
FIG. 1 is a photomicrograph of the components of the complex structure of the macroporous powder produced by the precipitation polymerization process in accordance with Example I, and illustrating the unit particles, agglomerates, and aggregates.
FIG. 2 is a photomicrograph of an agglomerate of FIG. 1 but shown on a larger scale.

Each figure in the drawing indicates in the upper left hand corner the magnification employed in producing the photomicrograph.

DETAILED DESCRIPTION OF THE INVENTION

Figure 3:
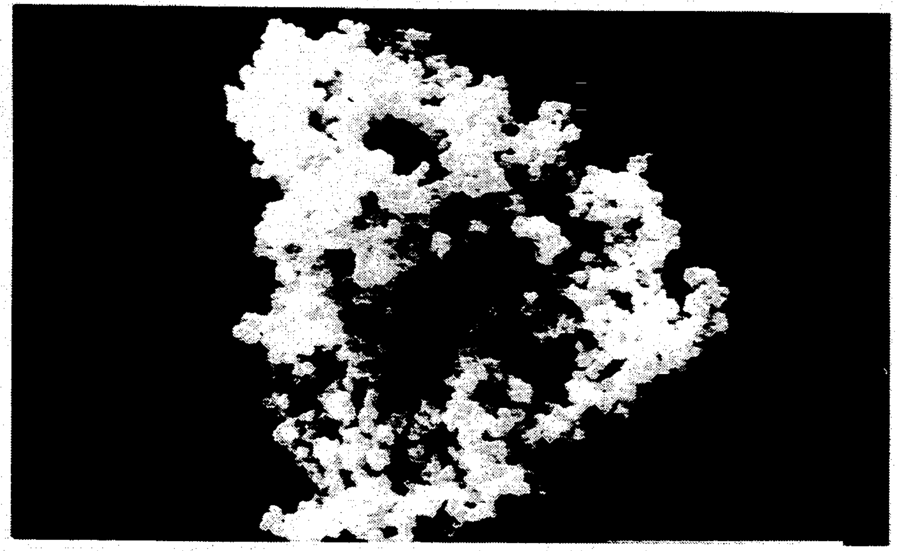
FIG. 3 is a photomicrograph of an aggregate of FIG. 1 but shown on a larger scale.

As should be apparent from a consideration of FIGS. 1–3, the polymeric material of the present invention is macroporous due to a complex arrangement of unit particles, agglomerates, and aggregates. As a result of this complex structure, the material possesses an inordinate amount of interstitial space and is a labyrinth of voids. Volatile ingredients entrapped within the void volume of the material are released by wicking to the surface and evaporate at a rate dependent upon such factors as temperature, vapor pressure, and surface area. Nonvolatile ingredients migrate to the surface by means of capillary action and are released on contact with another surface. Mechanical disruption may also be used to release the entrappad ingredient. The material is capable of wicking ingredients from another surface in the manner of a sponge. The material does not shrink or expand even though it is capable of adsorbing several times its own weight of an active ingredient. Since the process involved is adsorption in contrast to absorption, the properties of both the material and the active ingredient are not altered. Active ingredients are entrapped within the material in contrast to being encapsulated. Encapsulation connotes a complete enclosing of one material within another such as a shell formed around a core of liquid. Encapsulated ingredients are released by mechanical disruption of the shell or dissolution of the shell, and once the shell is disrupted the entire contents of the shell are extracted. With entrapment, however, the release of the entrappad ingredient is controlled or sustained by wicking, evaporation, and capillary action. In addition, the active ingredient is permitted a relatively unobstructed ingress and egress into and out of the labyrinth in entrapment type systems.

The hydrophobic macroporous material of the present invention can be generically described as a crosslinked polymer in particulate form capable of entrapping solids and liquids. The particles are free flowing discrete solids even when loaded with an active ingredient. One polymer representative of the materials contemplated by the present invention has the formula:

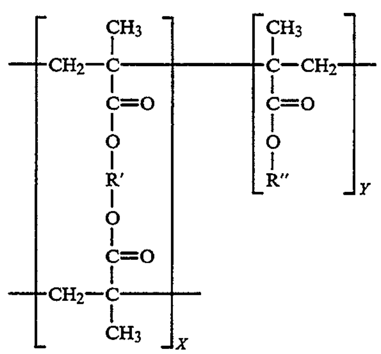

wherein the ratio of x to y is 80:20, R' is $—CH_2CH_2—$, and R'' is $—(CH_2)_{11}CH_3$.

This polymeric material is highly crosslinked and is a polymethacrylate. The material is manufactured by the Dow Corning Corporation, Midland, Mich., U.S.A., and sold under the trademark POLYTRAP. It is a low density, highly porous, free-flowing white particulate, and the particles are capable of adsorbing high levels of lipophilic liquids and some hydrophilic liquids while at the same time maintaining a free-flowing particulate character. The polymer can be formed by polymerizing a single polyunsaturated monomer such as ethylene glycol dimethacrylate or tetraethylene glycol dimethacrylate. The polymer may also be formed by polymerizing two monomers including a polyunsaturated monomer and a monounsaturated monomer such as lauryl methacrylate or 2-ethylhexyl methacrylate.

The polymer particles can be in the form of a bead in which case the bead has an average diameter of about ten microns to about one hundred-fifty microns. Alternatively, the polymer particles can be in the form of a powder and this powder is a combined system of particles. The system of powder particles includes unit particles of less than about one micron in average diameter, agglomerates of several fused unit particles of sizes in the range of about twenty to eighty microns in average diameter, and aggregates of clusters of several fused agglomerates of sizes in the range of about two-hundred to about twelve-hundred microns in average diameter. Whether the polymer is in the form of a spherical macroporous bead or in the form of the complex macroporous powder, the structure in accordance with this invention must be free of any "in situ" entrapped active ingredient.

A precipitation polymerization process is one method for producing the macroporous cross-linked polymer. In the process, there is polymerized one monounsaturated monomer and one polyunsaturated monomer in the presence of an excess of a volatile organic liquid which is a solvent for the monomers but not for the polymer. Polymerization of the monomers is initiated by means of a free radical generating catalytic compound which precipitates a polymer in the solvent in the form of a powder structure. A dry powder is formed by removing the volatile solvent from the precipitated polymeric powder leaving a structured submicron sized adsorbent. The most preferred solvent is isopropyl alcohol although other solvents such as ethanol, toluene, heptane, xylene, hexane, ethyl alcohol, and cyclohexane may also be employed. The monounsaturated monomer and the polyunsaturated monomer can be present in several mole ratios such as 20:80, 30:70, 40:60, or 50:50.

The process includes the step of stirring the monomers, the solvent, and the free radical generating catalytic compound during polymerization. The powder is dried by filtering excess solvent from the precipitated powder and the filtered powder is vacuum dried. The empty powder may then be used in this form or it can be formulated by "post adsorbing" the empty powder with various functional materials. In the present invention, the empty powder is the form employed in the antiperspirant products described herein.

Adsorption of active ingredients can be accomplished using a stainless steel mixing bowl and a spoon. The active ingredient is added to the empty dry powder and the spoon is used to gently fold the active into the powder. Low viscosity fluids may be adsorbed by addition of the fluids to a sealable vessel containing the powder and tumbling the materials until a consistency is achieved. More elaborate blending equipment such as ribbon or twin cone blenders can also be employed.

The following example illustrates one method for making an adsorbent powder of the type illustrated in FIGS. 1-3.

EXAMPLE I

A hydrophobic porous polymer was produced in a five hundred milliliter reactor equipped with a paddle type stirrer by mixing 13.63 grams of ethylene glycol dimethacrylate monomer which is equivalent to eighty mole percent, and 4.37 grams of lauryl methacrylate monomer which is equivalent to twenty mole percent. Isopropyl alcohol was added to the reactor as the solvent in the amount of 282 grams. The monomers were soluble in the solvent but not the precipitated polymer. The process can also be conducted using one polyunsaturated monomer instead of two monomers. The mixture including the monomers, the solvent, and 0.36 grams of the catalytic initiator benzoyl peroxide was purged with nitrogen. The system was heated with a water bath to sixty degrees Centigrade until polymerization was initiated and the temperature was increased to 70-75 degrees for six hours to complete polymerization. During this time the polymer precipitated from the solution. The polymerization produced unit particles of a diameter less than about one micron. Some of the unit particles adhered and fused together forming agglomerates twenty to eighty microns in diameter. Some of the agglomerates adhered and fused together forming aggregates of loosely held assemblies of agglomerates two to eight hundred microns in diameter. The mixture was filtered to remove excess solvent and a wet powder cake was tray dried in a vacuum oven. A dry hydrophobic polymeric powder consisting of unit particles, agglomerates, and aggregates was isolated.

The method of Example I is a precipitation polymerization technique. In accordance with this technique, monomers are dissolved in a compatible volatile solvent in which both monomers are soluble. Polymer in the form of a powder is precipitated and the polymer is insoluble in the solvent. No surfactant or dispersing aid is required. The materials produced are randomly shaped particles and not spheres or beads. The randomly shaped powder particulates include unit particles, agglomerates, and aggregates. The volatile solvent is removed leaving an empty dry powder. The empty dry powder is suitable for use in this condition in some applications or it may be "post adsorbed" with a variety of functional active ingredients for other applications.

Some unique features of the powder of Example I and. FIGS. 1-3 is its ability to adsorb liquids and yet remain free flowing. The material provides a regulated release of ingredients entrapped therein and has the capability of functioning as a carrier. The powders disappear when rubbed upon a surface. This phenomenon is due to the fact that large aggregates of the material scatter light rendering the appearance of a white particulate but when rubbed these large aggregates decrease in size approaching the range of visible light and hence seem to disappear. The materials possess utility in many diverse areas such as cosmetics and toiletries, household and industrial products, pesticide and pheromone carriers, and pharmaceuticals products for example.

The following example illustrates another precipitation polymerization process but in which an organic ester is entrapped "in situ" in the polymer.

EXAMPLE II

Seven grams of 2-ethylhexyl oxystearate was mixed with 1.5 grams of ethylene glycol dimethacrylate and 1.5 grams of lauryl methacrylate in a glass test tube. The solution was deaerated for five minutes and 0.1 milliliters of t-butyl peroctoate was added and mixed while heating to eighty degrees Centigrade in an oil bath. After twenty minutes the contents of the glass test tube solidified and the mixture was maintained at the same temperature for an additional hour to assure full polymerization. A heterogeneous white polymer resulted containing the entrapped ester.

The powder product of Example I differs from the powder product of Example II in that a volatile solvent is used in Example I and the solvent is removed resulting in a dry empty powder. In Example II a non-volatile functional material is polymerized "in situ" and remains entrapped in the powder product.

In contrast to Examples I and II, suspension polymerization is carried out in water. The monomers, the active ingredient, and the catalyst, are combined and form beads or droplets in the water and polymerization occurs within each bead. A surfactant or stabilizer such as polyvinyl pyrrolidone is required to prevent each individually formed bead and droplet from coalescing. The resulting beads with an active material entrapped therein include a substantially spherical outer crust or shell and an interior of macroporous structure. The bead is about ten microns in average diameter to about one hundred-fifty microns depending upon the rate of agitation employed during the process.

Example III illustrates a process for the production of beads by suspension polymerization and an organic ester is entrapped "in situ" within the beads.

Figure 4:
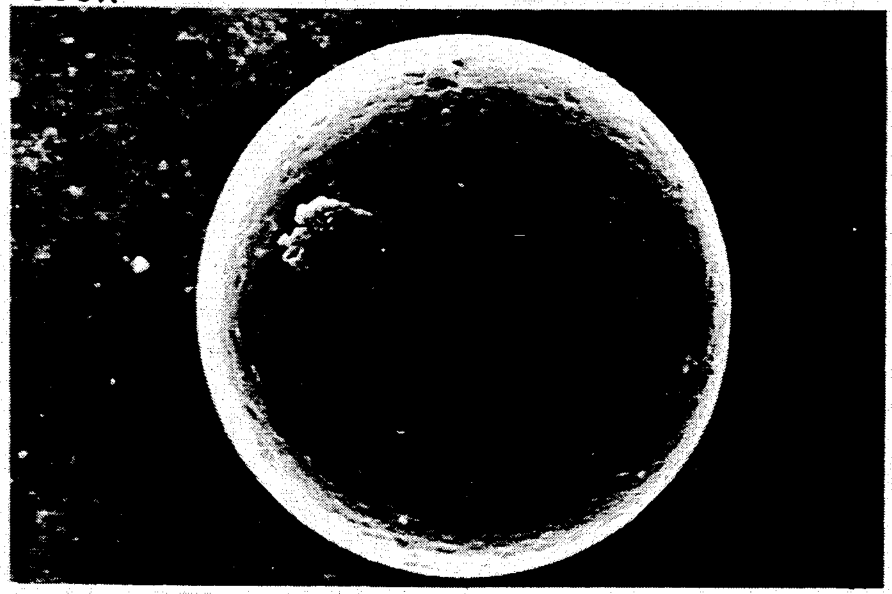
FIG. 4 is a photomicrograph of a polymer bead produced by suspension polymerization in accordance with Example III.
Figure 5:
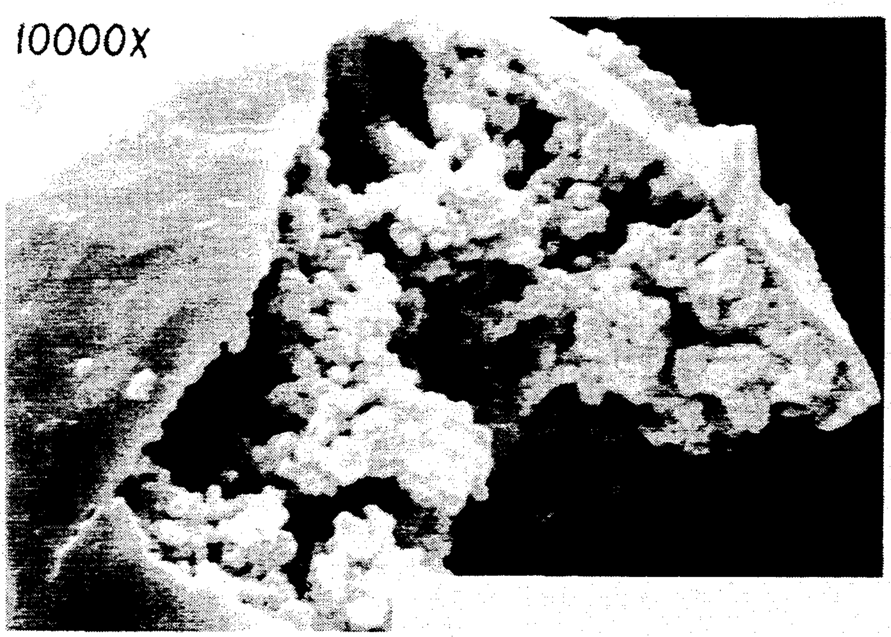
FIG. 5 is a photomicrograph of the bead of FIG. 4 on a larger scale and having a portion of the outer surface of the bead removed to reveal the interior macroporous structure of the bead.

EXAMPLE III 1.2 grams of polyvinyl pyrrolidone was dissolved in 1500 milliliters of water in a two liter three necked flask equipped with a stirrer, a thermometer and a nitrogen purge. A solution of 335 grams of 2-ethylhexyl oxystearate, 132 grams of ethylene glycol dimethacrylate, 33 grams of 2-etbylhexyl methacrylate, and five milliliters of t-butyl peroctoate was bubbled with nitrogen for five minutes. This mixture was slowly added to the stirred aqueous solution of polyvinyl pyrrolidone at twenty-two degrees Centigrade under nitrogen. The temperature was raised to eighty degrees with constant agitation and held until polymerization started in about fifteen minutes. The temperature was maintained at eighty degrees for an additional two hours to complete the reaction. White beads were collected by filtering off the supernatant liquid and dried to remove any excess water. The beads weighed 450 grams for a yield of ninety percent and were 0.25 to 0.5 millimeters in diameter. Such beads are shown in the drawings in FIGS. 4 and 5. Other protective colloids such as starch, polyvinyl alcohol, carboxymethyl cellulose, methyl cellulose; or inorganic divalent alkali metal hydroxides such as MgOH, may be used in place of the polyvinyl pyrrolidone suspending medium used in this example.

In Example III, macroporous polymers submicron in size are produced and polymerization is conducted in the presence of an active ingredient which does not dissolve or swell the resulting polymer. The monomers and the active ingredient are mutually soluble but insoluble in the aqueous suspending medium in which droplets are formed. Polymerization occurs within suspended droplets and beads or spheres are produced. The active ingredient which is polymerized "in situ" is entrapped and contained within the beads but the active ingredient is capable of being released. A volatile solvent can be substituted for the active ingredient removed leaving behind an empty porous polymer bead product free of "in situ" entrapped active materials.

Examples of polyunsaturated monomers suitable for use in accordance with the present invention are ethylene glycol dimethacrylate, triethylene glycol dimethacrylate, tetraethylene glycol dimethacrylate, trimethylolpropane ethoxylated triacrylate, ditrimethylolpropane dimethacrylate; propylene, dipropylene and higher propylene glycols; 1,3 butylene glycol dimethacrylate; 1,4 butanediol dimethacrylate; 1,6 hexanediol dimethacrylate, neopentyl glycol dimethacrylate, pentaerythritol dimethacrylate, dipentaerythritol dimethacrylate, bisphenol A dimethacrylate, divinyl and trivinylbenzene, divinyl and trivinyltoluene, triallyl maleate, triallyl phosphate, diallyl maleate, diallyl itaconate, and allyl methacrylate.

The monounsaturated monomers may include allyl methacrylates and acrylates having straight or branched chain alkyl groups with 1 to 30 carbon atoms preferably 5 to 18 carbon atoms. Preferred monomers include lauryl methacrylate, 2-ethylhexyl methacrylate, isodecylmethacrylate, stearyl methacrylate, hydroxyethyl methacrylate, hydroxypropyl methacrylate, diacetone acrylamide, phenoxyethyl methacrylate, tetrahydrofurfuryl methacrylate and methoxyethyl methacrylate. Many of the previously referred to patents contain other suitable monomers that can also be used. Highly crosslinked polymeric systems consisting of particles of submicron size can be prepared from only monomers having at least two polymerizable unsaturated bonds and containing no comonomers having monounsaturated moiety.

In the preferred embodiments of the present invention, the antiperspirant product includes about eighteen to fifty weight percent of an astringent antiperspirant compound, about ten to sixty-five weight percent of a volatile silicone carrier, and about three to about five weight percent of the hydrophobic macroporous polymer. Most preferably, the product includes twenty weight percent of astringent antiperspirant compound, and fifty to eighty weight percent of the volatile silicone. The volatile silicone carrier in accordance with the present invention includes low viscosity silicone fluids such as polydimethylcyclosiloxane. Such fluids have viscosities measured at twenty-five degrees Centigrade of less than about five centistokes. These volatile fluids have the formula $(CH_3)_2SiO_x$ in which x is an integer from three to eight. Representative volatile cyclic siloxanes are the tetramer octamethylcyclotetrasiloxane and the pentamer decamethylcyclopentasiloxane. The volatile silicone employed herein may also include mixtures of the tetramer and the pentamer. Linear volatile silicones may also be employed and such polysiloxanes have the repeating unit

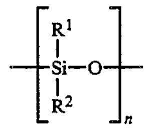

wherein n is an integer having a value greater than 1, $R^1$ is an alkyl radical containing 1 to 7 carbon atoms, inclusive, or a phenyl group, $R^2$ is hydrogen an alkyl radical containing 1 to 7 carbon atoms, inclusive, or a phenyl group. Illustrative of the linear volatile low viscosity polysiloxanes encompassed by the above formula is hexamethyldisiloxane. This linear siloxane has a viscosity of about 0.65 centistokes measured at twenty-five degrees Centigrade.

Any conventional astringent antiperspirant compound can be used in accordance with the present invention. In general, such materials comprise inorganic and organic salts of aluminum, zirconium, and zinc, and mixtures thereof. Representative compounds are described throughout the patent literature in U.S. Pat. No. 4,280,994, issued Jul. 28, 1981; U.S. Pat. No. 4,369,173, issued Jan. 18, 1983; U.S. Pat. No. 4,425,328, issued Jan. 10, 1984; U.S. Pat. No. 4,725,432, issued Feb. 16, 1988; and U.S. Pat. No. 4,822,603, issued Apr. 18, 1989. Examples of such astringent antiperspirant compounds are aluminum chloride, aluminum chlorohydrate, aluminum dichlorohydrate, aluminum-zirconium chlorohydrate, aluminum chlorohydrex, aluminum-zirconium trichlorohydrate, aluminum-zirconium pentachlorohydrate, aluminum-zirconium tetrachlorohydrex glycine, aluminum-zirconium octachlorohydrate, aluminum sesquichlorohydrate, aluminum sulfate, zinc sulfate, zirconium chlorohydrate, aluminum-zirconium chlorohydroglycine, zirconium hydroxychloride, zinc sulfocarbolate, aluminum bromide, zinc phenolsulfonate, and aluminum bromohydrate.

Emollients, perfumes, and other ingredients normally used in making antiperspirant products are well known in the art and are described throughout the patent literature in the previously mentioned U.S. Pat. Nos. 4,280,994; 4,425,328; 4,725,432; and 4,822,603.

The use of suspending agents in antiperspirant products is conventional in the art as represented by U.S. Pat. No. 4,904,463, issued Feb. 27, 1990. However, as noted in the '463 patent, the use of clay minerals such as hectorite and bentonire as a suspending agent requires that the clay mineral be treated with a cationic surfactant material to render the clay mineral hydrophobic. Ditallow dimethyl ammonium chloride is one cationic surfactant found most suitable for such treatments. In addition to requiring this pre-hydrophobing treatment, systems containing these clay minerals further require a separate activator such as ethanol or propylene carbonate which enables the hydrophobically treated clay material to suspend the antiperspirant compound in the carrier fluid. While such clay minerals have been found to be effective suspending agents in antiperspirant formulations, their hydrophobic pretreatment requirements and the necessity of employing an activator as an additional ingredient are distinct disadvantages. In contrast, the present invention provides an effective suspending agent for antiperspirant products which is inherently hydrophobic and hence there is no requirement for any pretreatment. In addition, the macroporous polymer described herein may be employed to suspend the antiperspirant compound without the requirement of an activator in order to render it effective.

It is also known that clay materials such as bentonite and hectorite when used in cosmetic and toiletry products suffer from the disadvantages of causing unpredictable and drifting viscosities because of variations in the clay products. Such materials have poor resuspendability in such products and are often responsible for less than adequate performance of these products due to compaction. On the other hand, the macroporous suspending agents of the present invention possess excellent suspension properties, exhibit little if Any compaction because of their macroporous construction, and are easily redispersed.

The following examples are set forth in order to illustrate the concepts embodied in accordance with the present invention.

EXAMPLE IV

There was combined four weight percent of the hydrophobic macroporous polymer powder of Example I, twenty weight percent of activated aluminum-zirconium hydroxychloride glycine, and seventy-six weight percent of a cyclic polydimethylsiloxane. These ingredients were mixed employing a homogenizer until a uniform blend was obtained. The blend was found to function as an effective roll-on antiperspirant formulation.

EXAMPLE V

There was combined 3.5 weight percent of the hydrophobic macroporous polymer powder of Example I, twenty weight percent of activated aluminum-zirconium hydroxychloride glycine, seventy-six weight percent of a cyclic polydimethylsiloxane, and 0.5 weight percent of a linear polydimethylsiloxane having a viscosity of one thousand centistokes measured at twenty-five degrees Centigrade. These ingredients were mixed employing a homogenizer until a uniform blend was obtained. The blend was found to function as an effective roll-on antiperspirant formulation.

Use of the powder material of Example I, which is free of "in situ" entrapped active ingredients, has significant advantages over use of the materials of Examples II and III which are "in situ" polymerized products containing entrapped active ingredients. Aside from the obvious physical differences in the materials, the empty powder of Example I is rigid and hard in comparison, and has the ability to effect the viscosity of the formulation. This provides the benefit of decreasing the settling of the antiperspirant compound with the result that there is created a more uniform distribution of the antiperspirant compound in and throughout the product. The empty powder material of Example I also decreases the whitening of films formed upon the skin when the stick product is applied in contrast to the softer materials of Examples II and III. This has the benefit of providing an improvement in the aesthetics upon application of products containing the macroporous empty powder materials of Example I. Because the empty powder material of Example I is free of "in situ" entrapped ingredients in contrast to the loaded materials of Examples II and III, the empty powder material of Example I possesses multitudinous voids. These voids create a more porous film when the product is applied to the skin. This has the benefit of increasing the availability of moisture to the water soluble antiperspirant compound in the product, with the result that there is established a more efficient transport of the antiperspirant compound to the sweat glands. In contrast to the "in situ" materials of Examples II and III, the empty powder of Example I has the ability to adsorb non-compatible components of antiperspirant products that would otherwise remain unsuspended.

It will be apparent from the foregoing that many other variations and modifications may be made in the compounds, compositions, and methods described herein without departing substantially from the essential features and concepts of the present invention. Accordingly, it should be clearly understood that the forms of the invention described herein are exemplary only and are not intended as limitations of the scope on the present invention.

That which is claimed is:

1. In an antiperspirant composition containing as components thereof at least one material selected from the group consisting of astringent antiperspirant compounds, a volatile carrier, a suspending agent, emollients, and perfumes, the improvement comprising incorporating into the composition as the suspending agent thereof a hydrophobic macroporous crosslinked polymer, the hydrophobic macroporous polymer being free of in situ entrapped active ingredients.

2. The composition of claim 1 wherein the polymer is formed of at least one polyunsaturated monomer.

3. The composition of claim 2 wherein the polyunsaturated monomer is selected from the group consisting of ethylene glycol dimethacrylate and tetraethylene glycol dimethacrylate.

4. The composition of claim 1 wherein the polymer is formed of at least one monounsaturated monomer and at least one polyunsaturated monomer.

5. The composition of claim 4 wherein the monounsaturated monomer is selected from the group consisting of lauryl methacrylate and 2-ethylhexyl methacrylate, and the polyunsaturated monomer is selected from the group consisting of ethylene glycol dimethacrylate and tetraethylene glycol dimethacrylate.

6. The composition of claim 1 in which the macroporous polymer is in the form of particles in the shape of a bead.

7. The composition of claim 6 in which the particles have an average diameter of about ten microns to about one hundred-fifty microns.

8. The composition of claim 1 in which the macroporous polymer is in the form of a powder, the powder being a combined system of polymer particles, the system of powder particles including unit particles of less than about one micron in average diameter, agglomerates of fused unit particles of sizes in the range of about twenty to eighty microns in average diameter, and aggregates of clusters of fused agglomerates of sizes in the range of about two-hundred to about twelve-hundred microns in average diameter.

9. The composition of claim 8 in which the polymer is a polymethacrylate.

10. The composition of claim 1 which includes about eighteen to about fifty weight percent of an astringent antiperspirant compound, about ten to about sixty-five weight percent of a volatile carrier, and about three to about five weight percent of the hydrophobic macroporous polymer.

11. The composition of claim 10 which includes twenty weight percent of astringent antiperspirant compound, and fifty to eighty weight percent of volatile silicone.

12. The composition of claim 1 in which the antiperspirant composition is anhydrous and is in the form of a roll-on product.

13. The composition of claim 1 in which the antiperspirant composition is in the form of an aerosol product.

14. The composition of claim 1 in which the hydrophobic macroporous crosslinked polymer has the formula:

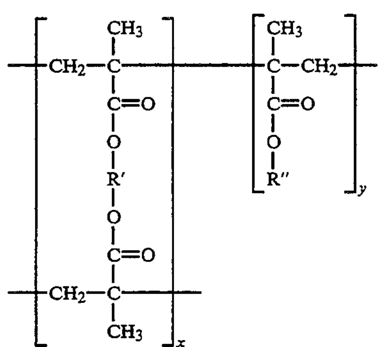

* * * * *